United States Patent
Barrick

(10) Patent No.: US 7,130,676 B2
(45) Date of Patent: *Oct. 31, 2006

(54) FLUOROSCOPIC IMAGE GUIDED ORTHOPAEDIC SURGERY SYSTEM WITH INTRAOPERATIVE REGISTRATION

(75) Inventor: Earl F Barrick, McLean, VA (US)

(73) Assignee: Sofamor Danek Holdings, Inc., Memphis, TN (US)

( * ) Notice: Subject to any disclaimer, the term of this patent is extended or adjusted under 35 U.S.C. 154(b) by 561 days.

This patent is subject to a terminal disclaimer.

(21) Appl. No.: 10/230,958

(22) Filed: Aug. 29, 2002

(65) Prior Publication Data

US 2003/0060703 A1    Mar. 27, 2003

Related U.S. Application Data

(63) Continuation of application No. 09/376,712, filed on Aug. 16, 1999, now Pat. No. 6,477,400.

(60) Provisional application No. 60/097,742, filed on Aug. 24, 1998, provisional application No. 60/097,183, filed on Aug. 20, 1998.

(51) Int. Cl.
*A61B 5/00* (2006.01)
(52) U.S. Cl. .................. 600/426; 600/427; 600/429; 606/130
(58) Field of Classification Search ........... 600/407, 600/426–427, 429; 606/130, 97; 378/205–207
See application file for complete search history.

(56) References Cited

U.S. PATENT DOCUMENTS

| | | | |
|---|---|---|---|
| 1,576,781 A | 3/1926 | Philips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Zehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,294,083 A | 12/1966 | Alderson |

(Continued)

FOREIGN PATENT DOCUMENTS

DE    3042343    6/1982

(Continued)

OTHER PUBLICATIONS

Adams et al., "Orientation Aid for Head and Neck Surgeons," Innov. Tech. Biol. Med., vol. 13, No. 4, 1992, pp. 409-424.

(Continued)

*Primary Examiner*—Ruth S. Smith
(74) *Attorney, Agent, or Firm*—Harness, Dickey & Pierce, P.L.C.

(57) ABSTRACT

A fluoroscopic image guided surgery system, comprising a C-arm fluoroscope for obtaining fluoroscopic images of an object bone, the C-arm fluoroscope including at least one set of emitters; a reference bar capable of attaching to an object bone, the reference bar including emitters; a surgical instrument for performing an operation, the instrument including emitters; a digitizer system in communication with the at least one set of emitters of the C-arm fluoroscope, the emitters of the reference bar, and the emitters of the surgical instrument so that the digitizer system can determine a position of each of the C-arm fluoroscope, the reference bar, and the surgical instrument; and a single fiducial marker for attachment to an object bone, the single fiducial marker being visible in the fluoroscopic images for determining a position of an object bone relative to the digitizer system.

65 Claims, 3 Drawing Sheets

U.S. PATENT DOCUMENTS

| | | |
|---|---|---|
| 3,367,326 A | 2/1968 | Frazier |
| 3,439,256 A | 4/1969 | Kähne et al. |
| 3,577,160 A | 5/1971 | White |
| 3,674,014 A | 7/1972 | Tillander |
| 3,702,935 A | 11/1972 | Carey et al. |
| 3,704,707 A | 12/1972 | Halloran |
| 3,868,565 A | 2/1975 | Kuipers |
| 3,941,127 A | 3/1976 | Froning |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,202,349 A | 5/1980 | Jones |
| 4,262,306 A | 4/1981 | Renner |
| 4,287,809 A | 9/1981 | Egli et al. |
| 4,314,251 A | 2/1982 | Raab |
| 4,317,078 A | 2/1982 | Weed et al. |
| 4,328,813 A | 5/1982 | Ray |
| 4,339,953 A | 7/1982 | Iwasaki |
| 4,358,856 A | 11/1982 | Stivender et al. |
| 4,368,536 A | 1/1983 | Pfeiler |
| 4,396,885 A | 8/1983 | Constant |
| 4,403,321 A | 9/1983 | DiMarco |
| 4,418,422 A | 11/1983 | Richter et al. |
| 4,422,041 A | 12/1983 | Lienau |
| 4,431,005 A | 2/1984 | McCormick |
| 4,485,815 A | 12/1984 | Amplatz |
| 4,543,959 A | 10/1985 | Sepponen |
| 4,548,208 A | 10/1985 | Niemi |
| 4,572,198 A | 2/1986 | Codrington |
| 4,584,577 A | 4/1986 | Temple |
| 4,613,866 A | 9/1986 | Blood |
| 4,618,978 A | 10/1986 | Cosman |
| 4,621,628 A | 11/1986 | Bludermann |
| 4,625,718 A | 12/1986 | Olerud et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,673,352 A | 6/1987 | Hansen |
| 4,706,665 A | 11/1987 | Gouda |
| 4,719,419 A | 1/1988 | Dawley |
| 4,722,056 A | 1/1988 | Roberts et al. |
| 4,722,336 A | 2/1988 | Kim et al. |
| 4,727,565 A | 2/1988 | Ericson |
| 4,737,794 A | 4/1988 | Jones |
| 4,737,921 A | 4/1988 | Goldwasser et al. |
| 4,750,487 A | 6/1988 | Zanetti |
| 4,771,787 A | 9/1988 | Wurster et al. |
| 4,791,934 A | 12/1988 | Brunnett |
| 4,793,355 A | 12/1988 | Crum et al. |
| 4,797,907 A | 1/1989 | Anderton |
| 4,803,976 A | 2/1989 | Frigg et al. |
| 4,821,206 A | 4/1989 | Arora |
| 4,821,731 A | 4/1989 | Martinelli et al. |
| 4,836,778 A | 6/1989 | Baumrind et al. |
| 4,845,771 A | 7/1989 | Wislocki et al. |
| 4,849,692 A | 7/1989 | Blood |
| 4,862,893 A | 9/1989 | Martinelli |
| 4,889,526 A | 12/1989 | Rauscher et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,099,845 A | 3/1992 | Besz et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,152,288 A | 10/1992 | Hoenig et al. |
| 5,154,717 A | 10/1992 | Matsen, III et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,228,442 A | 7/1993 | Imran |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,291,199 A | 3/1994 | Overman et al. |
| 5,295,483 A | 3/1994 | Nowacki et al. |
| 5,297,549 A | 3/1994 | Beatty et al. |
| 5,299,254 A | 3/1994 | Dancer et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |

| | | | | | | |
|---|---|---|---|---|---|---|
| 5,320,111 A | 6/1994 | Livingston | | 5,573,533 A | 11/1996 | Strul |
| 5,325,728 A | 7/1994 | Zimmerman et al. | | 5,575,794 A | 11/1996 | Walus et al. |
| 5,325,873 A | 7/1994 | Hirschi et al. | | 5,583,909 A | 12/1996 | Hanover |
| 5,329,944 A | 7/1994 | Fabian et al. | | 5,588,430 A | 12/1996 | Bova et al. |
| 5,333,168 A | 7/1994 | Fernandes et al. | | 5,592,939 A | 1/1997 | Martinelli |
| 5,353,795 A | 10/1994 | Souza et al. | | 5,595,193 A | 1/1997 | Walus et al. |
| 5,353,800 A | 10/1994 | Pohndorf et al. | | 5,596,228 A | 1/1997 | Anderton et al. |
| 5,353,807 A | 10/1994 | DeMarco | | 5,600,330 A | 2/1997 | Blood |
| 5,368,030 A | 11/1994 | Zinreich et al. | | 5,603,318 A | 2/1997 | Heilbrun et al. |
| 5,375,596 A | 12/1994 | Twiss et al. | | 5,617,462 A | 4/1997 | Spratt |
| 5,377,678 A | 1/1995 | Dumoulin et al. | | 5,617,857 A | 4/1997 | Chader et al. |
| 5,383,454 A | 1/1995 | Bucholz | | 5,619,261 A | 4/1997 | Anderton |
| 5,385,146 A | 1/1995 | Goldreyer | | 5,622,169 A | 4/1997 | Golden et al. |
| 5,385,148 A | 1/1995 | Lesh et al. | | 5,622,170 A | 4/1997 | Schulz |
| 5,386,828 A | 2/1995 | Owens et al. | | 5,627,873 A | 5/1997 | Hanover et al. |
| 5,389,101 A | 2/1995 | Heilbrun et al. | | 5,628,315 A | 5/1997 | Vilsmeier et al. |
| 5,391,199 A | 2/1995 | Ben-Haim | | 5,630,431 A | 5/1997 | Taylor |
| 5,394,457 A | 2/1995 | Leibinger et al. | | 5,636,644 A | 6/1997 | Hart et al. |
| 5,397,329 A | 3/1995 | Allen | | 5,638,819 A | 6/1997 | Manwaring et al. |
| 5,399,146 A | 3/1995 | Nowacki et al. | | 5,640,170 A | 6/1997 | Anderson |
| 5,400,384 A | 3/1995 | Fernandes et al. | | 5,642,395 A | 6/1997 | Anderton et al. |
| 5,402,801 A | 4/1995 | Taylor | | 5,643,268 A | 7/1997 | Vilsmeier et al. |
| 5,408,409 A | 4/1995 | Glassman et al. | | 5,645,065 A | 7/1997 | Shapiro et al. |
| 5,417,210 A | 5/1995 | Funda et al. | | 5,647,361 A | 7/1997 | Damadian |
| 5,419,325 A | 5/1995 | Dumoulin et al. | | 5,662,111 A | 9/1997 | Cosman |
| 5,423,334 A | 6/1995 | Jordan | | 5,664,001 A | 9/1997 | Tachibana et al. |
| 5,425,367 A | 6/1995 | Shapiro et al. | | 5,674,296 A | 10/1997 | Bryan et al. |
| 5,425,382 A | 6/1995 | Golden et al. | | 5,676,673 A | 10/1997 | Ferre et al. |
| 5,426,683 A | 6/1995 | O'Farrell, Jr. et al. | | 5,681,260 A | 10/1997 | Ueda et al. |
| 5,426,687 A | 6/1995 | Goodall et al. | | 5,682,886 A * | 11/1997 | Delp et al. .................. 600/407 |
| 5,427,097 A | 6/1995 | Depp | | 5,690,108 A | 11/1997 | Chakerers |
| 5,429,132 A | 7/1995 | Guy et al. | | 5,694,945 A | 12/1997 | Ben-Haim |
| 5,433,198 A | 7/1995 | Desai | | 5,695,500 A | 12/1997 | Taylor et al. |
| RE35,025 E | 8/1995 | Anderton | | 5,695,501 A | 12/1997 | Carol et al. |
| 5,437,277 A | 8/1995 | Dumoulin et al. | | 5,697,377 A | 12/1997 | Wittkampf |
| 5,443,066 A | 8/1995 | Dumoulin et al. | | 5,702,406 A | 12/1997 | Vilsmeier et al. |
| 5,443,489 A | 8/1995 | Ben-Haim | | 5,711,299 A | 1/1998 | Manwaring et al. |
| 5,444,756 A | 8/1995 | Pai et al. | | 5,713,946 A | 2/1998 | Ben-Haim |
| 5,445,144 A | 8/1995 | Wodicka et al. | | 5,715,822 A | 2/1998 | Watkins et al. |
| 5,445,150 A | 8/1995 | Dumoulin et al. | | 5,715,836 A | 2/1998 | Kliegis et al. |
| 5,445,166 A | 8/1995 | Taylor | | 5,718,241 A | 2/1998 | Ben-Haim et al. |
| 5,446,548 A | 8/1995 | Gerig et al. | | 5,722,594 A | 3/1998 | Barrick |
| 5,447,154 A | 9/1995 | Cinquin et al. | | 5,727,552 A | 3/1998 | Ryan |
| 5,448,610 A | 9/1995 | Yamamoto et al. | | 5,727,553 A | 3/1998 | Saad |
| 5,453,686 A | 9/1995 | Anderson | | 5,729,129 A | 3/1998 | Acker |
| 5,456,718 A | 10/1995 | Szymaitis | | 5,730,129 A | 3/1998 | Darrow et al. |
| 5,458,718 A | 10/1995 | Venkitachalam | | 5,730,130 A | 3/1998 | Fitzpatrick et al. |
| 5,464,446 A | 11/1995 | Dreessen et al. | | 5,732,703 A | 3/1998 | Kalfas et al. |
| 5,478,341 A | 12/1995 | Cook et al. | | 5,735,278 A | 4/1998 | Hoult et al. |
| 5,478,343 A | 12/1995 | Ritter | | 5,738,096 A | 4/1998 | Ben-Haim |
| 5,480,422 A | 1/1996 | Ben-Haim | | 5,741,214 A | 4/1998 | Ouchi et al. |
| 5,483,961 A | 1/1996 | Kelly et al. | | 5,742,394 A | 4/1998 | Hansen |
| 5,485,849 A | 1/1996 | Panescu et al. | | 5,744,953 A | 4/1998 | Hansen |
| 5,487,391 A | 1/1996 | Panescu | | 5,748,767 A | 5/1998 | Raab |
| 5,487,729 A | 1/1996 | Avellanet et al. | | 5,749,362 A | 5/1998 | Funda et al. |
| 5,487,757 A | 1/1996 | Truckai et al. | | 5,749,835 A | 5/1998 | Glantz |
| 5,490,196 A | 2/1996 | Rudich et al. | | 5,752,513 A | 5/1998 | Acker et al. |
| 5,494,034 A | 2/1996 | Schlondorff et al. | | 5,755,725 A | 5/1998 | Druais |
| 5,503,416 A | 4/1996 | Aoki et al. | | RE35,816 E | 6/1998 | Schulz |
| 5,513,637 A | 5/1996 | Twiss et al. | | 5,758,667 A | 6/1998 | Slettenmark |
| 5,515,160 A | 5/1996 | Schulz et al. | | 5,762,064 A | 6/1998 | Polyani |
| 5,517,990 A | 5/1996 | Kalfas et al. | | 5,767,699 A | 6/1998 | Hansen et al. |
| 5,531,227 A | 7/1996 | Schneider | | 5,769,789 A | 6/1998 | Wang et al. |
| 5,531,520 A | 7/1996 | Grimson et al. | | 5,769,861 A | 6/1998 | Vilsmeier |
| 5,542,938 A | 8/1996 | Avellanet et al. | | 5,775,322 A | 7/1998 | Silverstein et al. |
| 5,543,951 A | 8/1996 | Moehrmann | | 5,776,064 A | 7/1998 | Kalfas et al. |
| 5,546,940 A | 8/1996 | Panescu et al. | | 5,782,765 A | 7/1998 | Jonkman |
| 5,546,949 A | 8/1996 | Frazin et al. | | 5,787,886 A | 8/1998 | Kelly et al. |
| 5,546,951 A | 8/1996 | Ben-Haim | | 5,792,055 A | 8/1998 | McKinnon |
| 5,551,429 A | 9/1996 | Fitzpatrick et al. | | 5,795,294 A | 8/1998 | Luber et al. |
| 5,558,091 A | 9/1996 | Acker et al. | | 5,797,849 A | 8/1998 | Vesely et al. |
| 5,568,809 A | 10/1996 | Ben-Haim | | 5,799,055 A | 8/1998 | Peshkin et al. |
| 5,572,999 A | 11/1996 | Funda et al. | | 5,799,099 A | 8/1998 | Wang et al. |

| | | |
|---|---|---|
| 5,800,352 A | 9/1998 | Ferre et al. |
| 5,800,535 A | 9/1998 | Howard, III |
| 5,802,719 A | 9/1998 | O'Farrell, Jr. et al. |
| 5,807,252 A | 9/1998 | Hassfeld et al. |
| 5,810,728 A | 9/1998 | Kuhn |
| 5,810,735 A | 9/1998 | Halperin et al. |
| 5,823,192 A | 10/1998 | Kalend et al. |
| 5,823,958 A | 10/1998 | Truppe |
| 5,828,725 A | 10/1998 | Levinson |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,884,410 A | 3/1999 | Prinz |
| 5,891,034 A | 4/1999 | Bucholz |
| 5,891,157 A | 4/1999 | Day et al. |
| 5,904,691 A | 5/1999 | Barnett et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,981 A | 9/1999 | Cosman |
| 5,950,629 A | 9/1999 | Taylor et al. |
| 5,951,475 A | 9/1999 | Gueziec et al. |
| 5,954,647 A | 9/1999 | Bova et al. |
| 5,964,796 A | 10/1999 | Imran |
| 5,967,980 A | 10/1999 | Ferre et al. |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | VanDerBrug et al. |
| 6,016,439 A | 1/2000 | Acker |
| 6,019,725 A | 2/2000 | Vesely et al. |
| 6,021,343 A | 2/2000 | Foley et al. |
| 6,024,695 A | 2/2000 | Taylor et al. |
| 6,036,696 A | 3/2000 | Lambrecht et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,073,043 A | 6/2000 | Schneider |
| 6,104,944 A | 8/2000 | Martinelli |
| 6,118,845 A | 9/2000 | Simon et al. |
| 6,122,538 A | 9/2000 | Sliwa, Jr. et al. |
| 6,131,396 A | 10/2000 | Duerr et al. |
| 6,139,183 A | 10/2000 | Graumann |
| 6,148,117 A * | 11/2000 | Lopez et al. ............... 382/279 |
| 6,149,592 A | 11/2000 | Yanof et al. |
| 6,156,067 A | 12/2000 | Bryan et al. |
| 6,157,853 A | 12/2000 | Blume et al. |
| 6,161,032 A | 12/2000 | Acker |
| 6,167,145 A | 12/2000 | Foley et al. |
| 6,167,296 A | 12/2000 | Shahidi |
| 6,172,499 B1 | 1/2001 | Ashe |
| 6,175,756 B1 | 1/2001 | Ferre et al. |
| 6,223,067 B1 | 4/2001 | Vilsmeier et al. |
| 6,233,476 B1 | 5/2001 | Strommer et al. |
| 6,246,231 B1 | 6/2001 | Ashe |
| 6,273,896 B1 | 8/2001 | Franck et al. |
| 6,298,262 B1 | 10/2001 | Franck et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,381,485 B1 | 4/2002 | Hunter et al. |
| 6,424,856 B1 | 7/2002 | Vilsmeier et al. |
| 6,428,547 B1 | 8/2002 | Vilsmeier et al. |
| 6,434,415 B1 * | 8/2002 | Foley et al. ............... 600/425 |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,527,443 B1 | 3/2003 | Vilsmeier et al. |
| 6,551,325 B1 | 4/2003 | Neubauer et al. |
| 6,584,174 B1 | 6/2003 | Schubert et al. |
| 6,609,022 B1 | 8/2003 | Vilsmeier et al. |
| 6,611,700 B1 | 8/2003 | Vilsmeier et al. |
| 6,640,128 B1 | 10/2003 | Vilsmeier et al. |
| 6,694,162 B1 | 2/2004 | Hartlep |
| 6,701,179 B1 | 3/2004 | Martinelli et al. |

FOREIGN PATENT DOCUMENTS

| | | |
|---|---|---|
| DE | 3831278 A1 | 3/1989 |
| DE | 4233978 C1 | 4/1994 |
| EP | 964149 | 3/1975 |
| EP | 0 319 844 A1 | 1/1988 |
| EP | 0419729 A1 | 9/1989 |
| EP | 350996 | 1/1990 |
| EP | 0 651 968 A1 | 8/1990 |
| EP | 0 581 704 A1 | 7/1993 |
| EP | 0655138 B1 | 8/1993 |
| EP | 0894473 A2 | 1/1995 |
| FR | 79 04241 | 2/1979 |
| FR | 2417970 | 2/1979 |
| WO | WO 88/09151 | 12/1988 |
| WO | WO 89/05123 | 6/1989 |
| WO | WO 91/03982 | 4/1991 |
| WO | WO 94/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 96/11624 | 4/1996 |
| WO | WO 98/08554 | 3/1998 |
| WO | WO 98/38908 | 9/1998 |
| WO | WO 99/60939 | 12/1999 |
| WO | WO 01/30437 A1 | 5/2001 |

OTHER PUBLICATIONS

Benzel et al., "Magnetic Source Imaging: a Review of the Magnes System of Biomagnetic Technologies Incorporated," Neurosurgery, vol. 33, No. 2 (Aug. 1993), pp. 252-259.

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May 1992.

Foley, "The StealthStation: Three-Dimensional Image-Interactive Guidance for the Spine Surgeon," Spinal Frontiers, Apr. 1996, pp. 7-9.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Horner et al., "A Comparison of CT-Stereotaxic Brain Biopsy Techniques," Investigative Radiology, Sep.-Oct. 1984, pp. 367-373.

Kelly et al., "Computer-assisted stereotaxic laser resection of intra-axial brain neoplasms," Journal of Neurosurgery, vol. 64, Mar. 1986, pp. 427-439.

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Pelizzari et al., "Interactive 3D Patient-Image Registration," Information Processing in Medical Imaging, 12th International Conference, IPM '91, Jul. 7-12, 136-141 (A.C.F. Colchester et al. eds. 1991).

Schueler et al., "Correction of Image Intensifier Distortion for Three-Dimensional X-Ray Angiography," SPIE Medical Imaging 1995, vol. 2432, pp. 272-279.

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

Germano, "Instrumentation, Technique and Technology", Neurosurgery, vol. 37, No. 2, Aug. 1995, pp. 348-350.

Hatch, et al., "Reference-Display System for the Integration of CT Scanning and the Operating Microscope", Proceedings of the Eleventh Annual Northeast Bioengineering Conference, May 1985, pp. 252-254.

Dams, L., Knepper, A., Krybus, W., Meyer-Ebrecht, D., Pfeifer, G., Ruger, R., Witte, M., Aide au Reperage Tridimensional pour la Chirurgie de la Base du Crane, Innov. Tech. Biol. Med., vol. 13, No. 4, 1992, pp. 409-424.

Barrick, E.F., "Journal of Orthopaedic Trauma: Distal Locking Screw Insertion Using a Cannulated Drill Bit: Technical Note," Raven Press, vol. 7, No. 3, 1993, pp. 248-251.

Barrick, et al., "Prophylactic Intramedullary Fixation of the Tibia for Stress Fracture in a Professional Athlete," Journal of Orthopaedic Trauma, vol. 6, No. 2, pp. 241-244 (1992).

Barrick, et al., "Technical Difficulties with the Brooker-Wills Nail in Acute Fractures of the Femur," Journal of Orthopaedic Trauma, vol. 4, No. 2, pp. 144-150 (1990).

Batnitzky, S., Price, H.I., Lee, K.R., Cook, P.N., Cook, L.T., Fritz, S.L., Dwyer, S.J. Watts, C., Three-Dimensional Computer Reconstructions of Brain Mesions from Surface Contours Provided by Computed Tomography: A Prospectus, Neurosurgery, vol. 11, No. 1, Part 1, 1982, pp. 73-84.

Bouazza-Marouf, et al., "Robotic-Assisted Internatl Fixation of Fermoral Fractures," IMECHE., pp. 51-58 (1995).

Champleboux, G., Utilisation de Fonctions Splines pour la Mise au Point D'un Capteur Tridimensionnel sans Contact, Quelques Applications Medicales, Jul. 1991.

Cinquin, P., et al., "Computer Assisted Medical Interventions," IEEE Engineering in Medicine and Biology, May/Jun. 1995, pp. 254-263.

Cinquin, P., Lavallee, S., Demongeot, J., Computer Assisted Medical Interventions, International Advanced Robotics Programme, Sep. 1989, pp. 63-65.

Clarysse, P., Gibon, D., Rousseau, J., Blond, S., Vasseur, C., Marchandise, X., A Computer-Assisted System for 3-D Frameless Localization in Stereotaxic MRI, IEEE Transactions on Medical Imaging, vol. 10, No. 4, Dec. 1991, pp. 523-529.

Colchester, A.C.F., Hawkes, D.J., Information Processing in Medical Imaging, Lecture Notes in Computer Science, 12th International Conference, IPMI, Jul. 1991, pp. 136-141.

Feldmar, J., et al., "3D-2D Projective Registration of Free-Form Curves and Surfaces," Rapport de recherche (Inria Sophia Antipolis), 1994, pp. 1-44.

Foley, J.D., Van Dam, A., Fundamentals of Interactive Computer Graphics, The Systems Programming Series, Chapter 7, Jul. 1984, pp. 245-266.

Foley, K.T., Smith, K.R., Bucholz, R.D., Image-guided Intraoperative Spinal Localization, Intraoperative Neuro-protection, Chapter 19, 1996, pp. 325-340.

Gildenberg, P.L., Kaufman, H.H., Murthy, K.S. Calculation of Stereotactic Coordinates from the Computed Tomographic Scan, Neurosurgery, vol. 10, No. 5, May 1982, pp. 580-586.

Gonzalez, R.C., Digital Image Fundamentals, Digital Image Processing, Second Edition, 1987, pp. 52-54.

Gottesfeld Brown, L.M., et al., "Registration of Planar Film Radiographs with Computer Tomography," Proceedings of MMBIA, Jun. '96, pp. 42-51.

Gueziec, A.P., et al., "Registration of Computer Tomography Data to a Surgical Robot Using Fluoroscopy: A Feasiblity Study," Computer Science/Mathematics, Sep. 27, 1996, 6 pages.

Hamadeh, A., et al., "Automated 3-Dimensional Computer Tomographic and Fluoroscopic Image Registration," Computer Aided Surgery (1998), 3:11-19.

Hamadeh, A., et al., "Towards Automatic Registration Between CT and X-ray Images: Cooperation Between 3D/2D Registration and 2D Edge Detection," MRCAS '95, pp. 39-46.

Hatch, J.F., Reference-Display System for the Integration of CT Scanning and the Operating Microscope, Thesis, Thayer School of Engineering, Oct. 1984, pp. 1-189.

Henderson, J.M., Smith, K.R., Bucholz, R.D., An Accurate and Ergonomic Method of Registration for Image-guided Neurosurgery, Computerized Medical Imaging and Graphics, vol. 18, No. 4, Jul.-Aug. 1994, pp. 273-277.

Hoerenz, P., The Operating Microscope I., Optical Principles, Illumination Systems, and Support Systems, Journal of Microsurgery, vol. 1, 1980, pp. 364-369.

Hofstetter, R., et al., "Fluoroscopy Based Surgical Navigation-Concept and Clinical Applications," Computer Assisted Radiology and Surgery, 1997, pp. 956-960.

Hounsfield, G.N., Computerized transverse axial scanning (tomography): Part I. Description of system, British Journal of Radiology, vol. 46, No. 552, Dec. 1973, pp. 1016-1022.

Jacques, S., Sheldon, C.H., McCann, G.D., A Computerized Microstereotactic Method to Approach, 3-Dimensionally Reconstruct, Remove and Adjuvantly Treat Small CNS Lesions, Applied Neurophysiology, vol. 43, 1980, pp. 176-182.

Jacques, S., Sheldon, C.H., McCann, G.D., Freshwater, D.B., Rand, R., Computerized three-dimensional stereotaxic removal of small central nervous system lesion in patients, J. Neurosurg., vol. 53, Dec. 1980, pp. 816-820.

Joskowicz, L., et al., "Computer-Aided Image-Guided Bone Fracture Surgery: Concept and Implementation," CAR '98, pp. 710-715.

Kelly, P.J., Kall, B., Goerss, S., Alker, G.J., Jr., Precision Resection of Intra-Axial CNS Lesions by CT-Based Stereotactic Craniotomy and Computer Monitored CO2 Laser, Acta Neurochirurgica, vol. 68, 1983, pp. 1-9.

Lavallee, S., A New System for Computer Assisted Neurosurgery, IEEE Engineering in Medicine & Biology Society 11th Annual International Conference, 1989, pp. 0926-0927.

Lavallee, S., Brunie, L., Mazier, B., Cinquin, P., Matching of Medical Images for Computed and Robot Assisted Surgery, IEEE EMBS, Orlando, 1991.

Lavallee, S., Cinquin, P., Demongeot, J., Benabid, A.L., Marque, I., Djaid, M., Computer Assisted Interventionist Imaging: The Instance of Stereotactic Brain Surgery, North Holland MEDINFO 89, Part 1, 1989, pp. 613-617.

Lavallee, S., Cinquin, P., Demongeot, J., Benabid, A.L., Marque, I., Djaid, M., Computer Assisted Driving of a Needle into the Brain, Proceedings of the International Symposium: CAR 89, pp. 416-420.

Lavallee, S., Szeliski, R., Brunie, L., Matching 3-D Smooth Surfaces with Their 2-D Projections using 3-D Distance Maps, SPIE, vol. 1570, Geometric Methods in Computer Vision, 1991, pp. 322-336.

Lavalle, S., et al., "Image guided operating robot: a clinical application in steroetactic neurosurgery," Proceedings of the 1992 IEEE International Conference on Robotics and Automation, May 1992, pp. 618-624.

Leksell, L., Jernberg, B., Steretaxis and Tomography—A Technical Note, ACTA Neurochirurgica, vol. 52, 1980, pp. 1-7.

Lemieux, L., et al., "A Patient-to-Computer-Tomography Image Registration Method Based on Digitally Reconstructed Radiographs," Med. Phys. 21 (11), Nov. 1994, pp. 1749-1760.

Levin, D.N., Hu, X., Tan, K.K., Galhotra, S., Pelizzari, C.A., Chen, G.T.Y., Beck, R.N., Chen, C., Cooper, M.D., Mullan, J.F., Hekmatpanah, J., Spire, J., The Brain: Integrated Three-dimensional Display of MR and PET Images, Radiology, vol. 172, No. 3, Sep. 1989, pp. 783-789.

Mazier, B., Lavallee, S., Cinquin, P., Chirurgie de la Colonne Vertebrale Assistee par Ordinateur: Application au Vissage Pediculaire, Innov. Tech. Biol. Med., vol. 11, No. 5, 1990, pp. 559-566.

Mazier, B., Lavallee, S., Cinquin, P., Computer Assisted Interventionist Imaging: Application to the Vertebral Column Surgery, Annual International Conference of the IEEE Engineering in Medicine and Biology Society, vol. 12, No. 1, 1990, pp. 0430-0431.

PCT International Search Report, PCT/US99/14565, Oct. 20, 1999.

Pelizzari, C.A., Chen, G.T.Y., Halpern, H., Chen, C.T., Cooper, M.D., No. 528—Three Dimensional Correlation of PET, CT and MRI Images, The Journal of Nuclear Medicine, vol. 28, No. 4, Apr. 1987, p. 682.

Pelizzari, C.A., Chen, G.T.Y., Spelbring, D.R., Weichselbaum, R.R., Chen, C., Accurate Three-Dimensional Registration of CT, PET, and/or MR Images of the Brain, Journal of Computer Assisted Tomography, Jan./Feb. 1989, pp. 20-26.

Philips, R., et al., "Images Guided Orthopaedic Surgery Design and Analysis," Trans Inst MC, vol. 17, No. 5, 1995, pp. 251-264.

Potamianos, P., et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt, H.F., Landolt, H., CT-Guided "Real Time" Stereotaxy, ACTA Neurochirurgica, 1989.

Roberts, D.W., Strohbehn, J.W., Hatch, J.F., Murray, W., Kettenberger, H., A frameless stereotaxic integration of computerized tomographic imaging and the operating microscope, J. Neurosurg., vol. 65, Oct. 1986, pp. 545-549.

Rosenbaum, A.E., Lunsford, L.D., Perry, J.H., Computerized Tomography Guided Stereotaxis: A New Approach, Applied Neurophysiology, vol. 43, No. 3-5, 1980, pp. 172-173.

Sautot, Pascal Phillippe, "Vissage Pediculaire Assiste Par Ordinateur," Sep. 20, 1994.

Selvik, G., et al., "A Roentgen Stereophotogrammetric System," Acta Radiologica Diagnosis, 1983, pp. 343-352.

Shelden, C.H., McCann, G., Jacques, S., Lutes, H.R., Frazier, R.E., Katz, R., Kuki, R., Development of a computerized microstereotaxic method for localization and removal of minute CNS lesions under direct 3-D vision, J. Neuro-surg., vol. 52, 1980, pp. 21-27.

Smith, K.R., Bucholz, R.D., Computer Methods for Improved Diagnostic Image Display Applied to Stereotactic Neurosurgery, Automedical, vol. 14, 1992, pp. 371-382.

Viant, W.J., et al., "A Computer Assisted Orthopaedic System for Distal Locking of Intramedullary Nails," Proc. of MediMEC '95, Bristol, 1995, pp. 86-91.

Watanabe, E., Watanabe, T., Manaka, S.,Mayanagi, Y., Takakura, K., Three-Dimensional Digitizer (Neuronavigator): New Equipment for Computed Tomography-Guided Stereotaxic Surgery, Surgical Neurology, vol. 27, No. 6, Jun. 1987, pp. 543-547.

Watanabe, H., Neuronavigator, Igaku-no-Ayumi, vol. 137, No. 6, May 10, 1986, pp. 1-4.

* cited by examiner

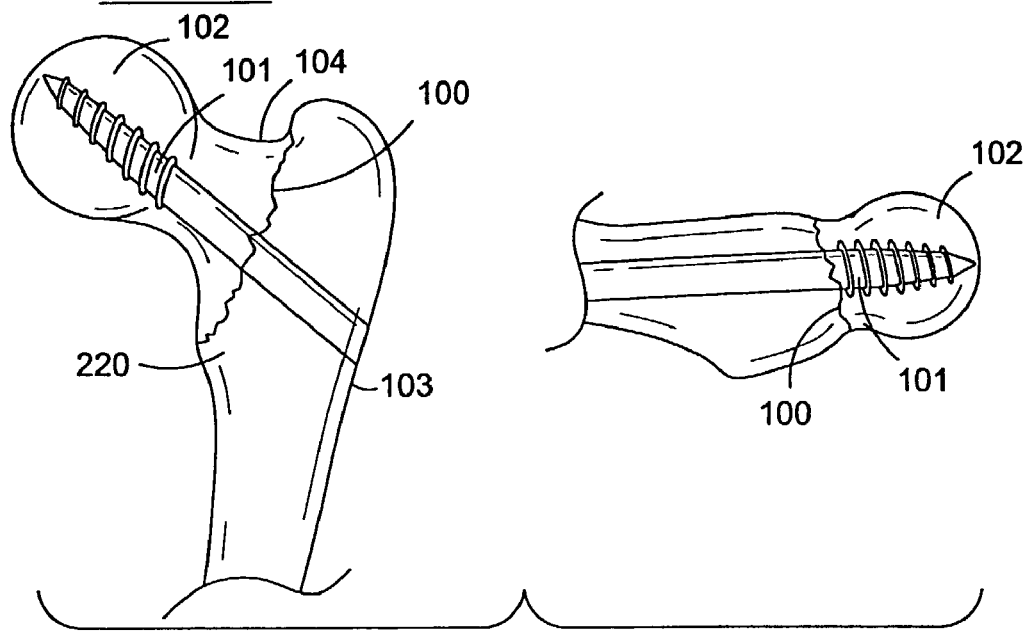
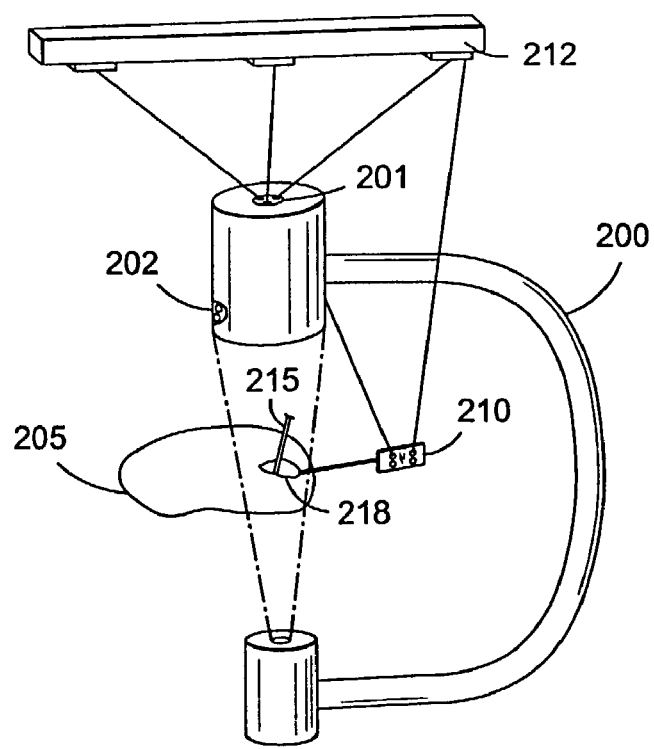

FLUOROSCOPIC IMAGE GUIDED ORTHOPAEDIC SURGERY SYSTEM WITH INTRAOPERATIVE REGISTRATION

CROSS-REFERENCE TO RELATED APPLICATIONS

This application is a continuation of U.S. patent application Ser. No. 09/376,712, filed on Aug. 16, 1999, now U.S. Pat. No. 6,477,400, issued on Nov. 5, 2002, which claims the benefit of both U.S. Provisional Application Ser. No. 60/097,742, filed on Aug. 24, 1998 and U.S. Provisional Application Ser. No. 60/097,183, filed on Aug. 20, 1998.

BACKGROUND OF THE INVENTION

In orthopaedic surgery it is often necessary to insert a guide pin for a cannulated screw, drill bit, or other screw (hereafter referred to as a fixation device) into a bone at a predetermined trajectory. Pre-operative planning depends on two-dimensional radiographic images which typically consist of two views taken at approximately right angles to one another. From these two views it is possible to determine the shape and structure of a long bone. Using that method, the path of insertion for a guide pin for a cannulated screw, drill bit, or screw is accurately determined. However, in practice the actual aiming of a fixation device is an inaccurate art, as the object bone is often seen only at one surface or is not seen at all and, therefore, positioning is dependent on fluoroscopic visualization. This method is also time consuming as the C-arm images must be taken separately and the drapes must be rearranged each time an image is taken. As bony tissue is unyielding, the track of the pin or drill bit is determined by the angular approach before entering the object bone. This angular approach is difficult to determine under normal circumstances and often multiple attempts are needed, as feedback is obtained from repeated fluoroscopic images. Existing methods of calculating the proper angle of guide pin for a cannulated hip screw insertion for hip pinning involve placing data manually into a computer program, which in turn outputs an angle of guide pin for a cannulated hip screw insertion.

Radiation exposure is a necessary part of any procedure for calculating the proper angle of a guide pin, drill bit, or screw insertion. Radiation exposure is considered to be a hazard. Ionizing radiation has no safe threshold of exposure below which it ceases to have adverse effects, although an arbitrary level is assumed. There has been a recent upward revision of risk estimates of radiation exposure, but absolute levels of safe exposure remain unknown. Exposure to the surgical team as well as the patient during orthopaedic procedures using fluoroscopy is a universal concern. Consequently, a reduction in the amount of radiation exposure is highly desirable.

Operative stereotactic localization using either frames or three-dimensional digitizers is currently being used in neurosurgery or otoloaryngology. Those methods require the use of computed axial tomography (CT) or magnetic resonance imaging (MRI) prior to surgery. They also involve placing markers on the scalp prior to the imaging study of the head. The markers must be left in the same position until surgery is performed in order to confirm intraoperative registration. Such imaging studies are routinely performed for most intracranial procedures but are impractical for most orthopaedic procedures, especially those involving long bones. A probe marked with light emitting diodes (LEDs) or other digitizing emitters is used to localize these markers or pins using a three-dimensional digitizing device at the time of surgery. A disadvantage of this system is that the images are normally obtained hours before use; thus, the images used are not up to date (real time) and are often not reflective of the current condition of the object bone.

Registration markers cannot be used on the outside of the body in most orthopaedic cases as the skin does not adhere to the underlying bone. Pre-operative registration for robotic placement of the femoral components for total hip arthroplasty requires the use of a separate procedure to insert screws for such markers. Such a separate procedure is highly impractical for routine orthopaedic procedures.

An alternative method of registration for image guided surgery requires wide operative exposure, such as in pedicle screw insertion in spine surgery. The various fiducials are determined by touching prominent or distinctive anatomic points with a digitizing probe as employed by the stereotactic localization system. Furthermore, the system also requires preoperative computed axial tomography.

A system using fluoroscopic images to guide the insertion of a fixation device employs tracking with a three-dimensional optical digitizer. This optical digitizer is used to determine the position in six degrees of freedom of a portable fluoroscopy machine ("C-arm fluoroscope") and the object region of the skeleton. Light emitting diodes ("LEDs") are placed in distinctive patterns on the C-arm. Another set of LEDs are attached to the bone with a percutaneous screw device, such as a reference bar. A computer program records these positions in relation to an optical position sensor.

X-rays are then taken with the C-arm fluoroscope with the two positions of the tube at approximate right angles to one another. The optical position sensor can thus determine where the C-arm is positioned in relation to LED markers attached to the reference bar attached to the object section of the skeleton. The exact position is determined by using two-dimensional image registration, matching the outline of the bone in two planes. In this system, three or more distinctly shaped radiographic markers are attached to threaded tipped registration pins inserted percutaneously. Thus, the object portion of the skeleton is localized in six degrees of freedom by the optical digitizer.

The computer program relates the position of the object bone with or without fiducial markers in the two fields to determine the exact relative position of the object bone seen on the two images. Once those two images are displayed on monitors, no further x-rays are needed. Thus, a substantial reduction in the amount of ionizing radiation results. The images displayed are those familiar to the surgeon but with the usual distortion eliminated.

A drill with attached LEDs inserts the fixation device in the position in the bone that the surgeon chooses based on the supplied information. The three-dimensional optical digitizer determines the position of the drill in relation to the optical digitizer camera and the object section of the skeleton with its fiducials. A graphic display of the fixation device of predetermined length is then overlaid on the images of the object bone in near real time. Thus, the position of the inserted pin or drill bit can be adjusted immediately.

SUMMARY OF THE INVENTION

The present invention allows an orthopaedic surgeon to safely determine the precise trajectory of insertion of a fixation device into an object bone and to check the accuracy of the procedure using real time feedback.

The present invention remedies the disadvantages of the prior art system of using fluoroscopic images and an optical digitizer to localize the object bone and the track of the intended fixation device.

The same three-dimensional optical digitizer is used to determine the position in six degrees of freedom of a portable fluoroscopy machine (C-arm fluoroscope) and the object region of the skeleton. Light emitting diodes (LEDs) are placed in distinctive patterns on the C-arm and attached to the bone, the latter with a percutaneous screw device, such as a reference bar. A computer program records these positions in relation to an optical position sensor.

X-rays are then taken with the C-arm fluoroscope with the two positions of the tube at approximate right angles to one another. The optical position sensor can thus determine where the C-arm is positioned in relation to LED markers attached to the reference bar attached to the object section of the skeleton. The exact position is determined by using two-dimensional image registration, matching the outline of the bone in two planes.

The difference from prior art is that, in this invention, distinctly shaped radiographic markers are not required to match the position of the object bone with the image thereof. Matching, or registration, is performed by a single registration pin or other object that is seen on both x-ray views. The spherical shape of the femoral head may be used to increase the accuracy of the registration if the invention is used for hip surgery. When used for inserting distal locking screws for intramedullary nails, the presence of the nail alone with the holes for the interlocking screws can be used as fiducial reference marker. This method of image registration is clearly superior to the use of three special registration pins with specialized markers.

The fixation device can then be inserted using a drill or drill guide that has attached LEDs that serve as means to localize it in six degrees of freedom. The graphic representation of the guide pin for a cannulated screw, drill bit, or extended projection of the drill guide positioned appropriately on the pair of monitors can be used to determine the correct trajectory.

Accurate localization of a hip screw in the femoral head has been shown in an important clinical study to result in much superior results than if the screw is placed eccentrically. Accurate aiming of an interlocking screw in an intramedullary nail is difficult to obtain using all current techniques. It is improved by this invention such that operative time and radiation are markedly reduced.

This invention has the advantage of simplifying the operation and making it more acceptable to use computer assisted surgery to improve accuracy.

BRIEF DESCRIPTION OF THE DRAWINGS

FIG. 1 is an illustration of anterior and lateral x-ray views of the proximal femur with an intertrochanteric fracture with a hip screw in optimal position.

FIGS. 2A & 2B are perspective illustrations of the intraoperative setting showing the C-arm fluoroscope, an optical digitizer camera, and the object body.

DETAILED DESCRIPTION OF THE PREFERRED EMBODIMENTS

Figure 2B:
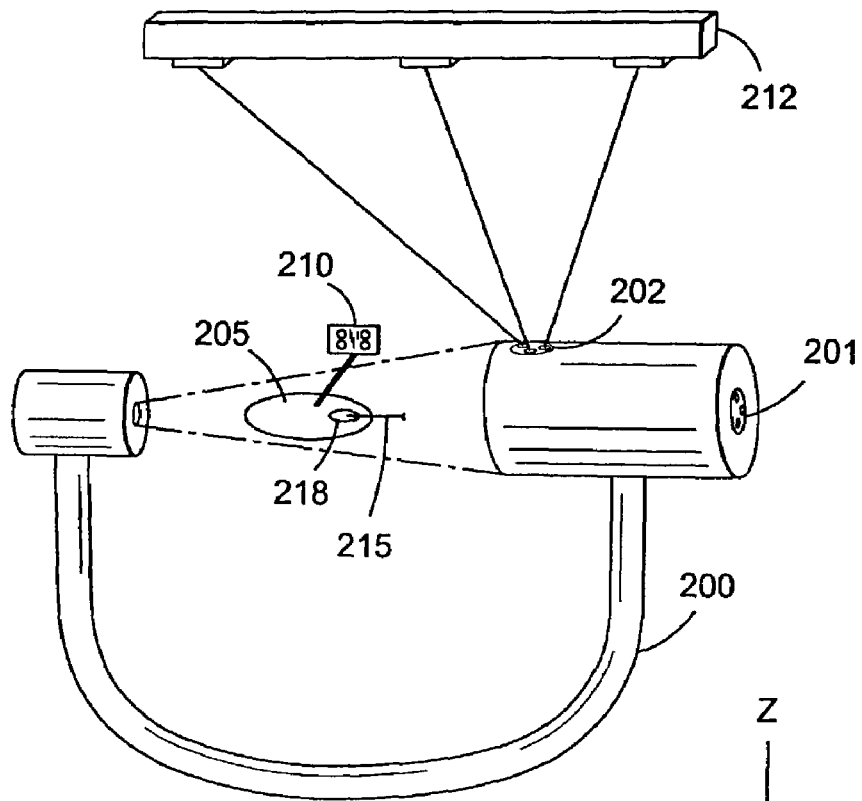
Figure 4:
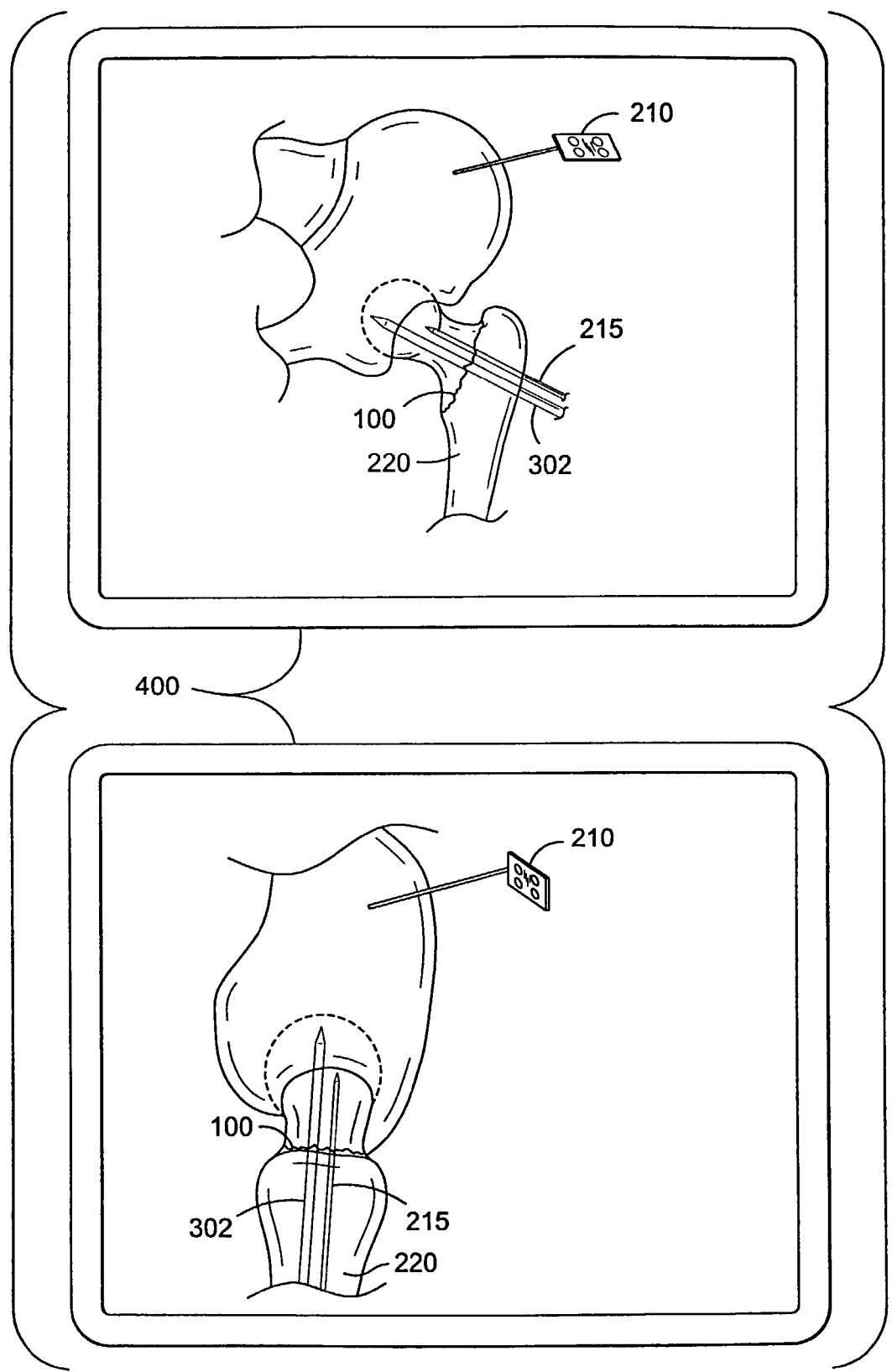
FIG. 4 is an illustration of a pair of computer monitor screens with radiographic images of the object bone at positions approximately 90 degrees to one another, with a single registration pin and a reference bar in place, and with the graphic image of a guide pin 302 for a cannulated hip screw superimposed.

The operation for the internal fixation of intertrochanteric hip fracture 100 requires a guide pin for a cannulated hip screw, and subsequently cannulated screw 101, to be placed into femoral head 102 from lateral cortex 103 of proximal femur 220 via femoral neck 104, as illustrated in FIG. 1. Guide pin 302 for cannulated hip screw 101 determines the position of cannulated screw 101. The ideal position of the guide pin for a cannulated hip screw, and thus screw 101, is entirely within bone. The end of the pin, and screw 101, is best positioned very near the subcortical bone but should not penetrate the cortex and thus enter the hip joint. The best results of an intertrochanteric fracture 100 must have been shown to occur when large screw 101 used is in the center of the femoral head at the subcortical bone. This position is normally obtained by placing the guide pin for a cannulated hip screw by estimation and by following its course on entry with repeated x-rays views in two planes. C-arm fluoroscope 200, as seen in FIG. 2, must be moved from one position of the other. Repeated attempts may be needed before the optimal position of guide pin 302, as seen in FIG. 4, for a cannulated hip screw can be obtained. Operating time and radiation exposure would be reduced by using image guided surgery. The accuracy and thus long term results would be improved.

In this system of fluoroscopic image guided orthopaedic surgery with intraoperative registration, light emitting diodes (LEDs) are attached to portable C-arm fluoroscopy 200 at two sites. One LED 201 is placed to determine the position of C-arm 200 when in the upright position as in FIG. 2A, which corresponds to the anteroposterior x-ray view when the patient 205 is supine. Another LED 202 is located so that it is seen by optical digitizer camera 212 when C-arm 200 is horizontal as in FIG. 2B, corresponding to the lateral x-ray view.

Patient 205 is lying supine in traction on a fracture table during the procedure. After appropriate sterile preparation, reference bar 210 with LEDs is inserted through a small incision into ilium 218. The optical digitizer software is programmed to recognize the region of the skeleton attached to reference bar 210 as a rigid body. The rigid body computer model thus remains immobile, and the other objects with LEDs attached move in relation to this rigid body. Femur 220 must remain immobile in relation to ilium 218, which is usually the case. FIG. 4 illustrates x-ray views seen with the fluoroscope.

Then proximal femur 220 is exposed through a routine lateral incision. Registration pin 215 is then inserted in proximal femur 220. X-rays at approximate right angles are then taken in the standard anteroposterior and lateral views. When C-arm 200 is in the upright position (FIG. 2A), LEDs 201 facing optical digitizer camera 212 indicate to the computer where C-arm 200 is in three dimensional space. Thus the computer can calculate the plane in which body 205 lies—in relation to reference bar 210. When C-arm 200 is in the horizontal position (FIG. 2B), LEDs 202 are now facing optical digitizer camera 212 and indicate again where C-arm 200 is in three dimensional space when in this position. The computer can then calculate exactly where body 205 and femur 220 seen on x-ray are in relation to optical digitizer camera 212. This calculation is possible with registration pin 215 and femur 220 now being recorded in two positions. The method of finding the position of registration pin 215 is a type of image registration.

Figure 3:
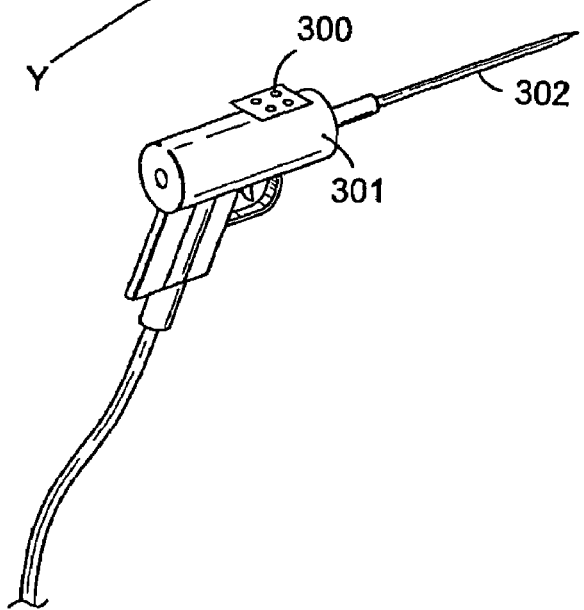
FIG. 3 is an illustration of a drill with mounted light emitting diodes.

LEDs 300 are mounted on the body of drill 301 as shown in FIG. 3. Guide pin 302 for cannulated hip screw 101 is placed in position into drill 301.

The signals emitted from LEDs 300 on drill 301 are received by optical digitizer camera 212 when placed in the operating field. The computer can then determine the position of drill 301 to reference bar 210 and thus to femur 220. A graphic image of guide pin 302 for a cannulated hip screw can then be displayed on each monitor 400 as seen in FIG. 4 to show the relationship of guide pin 302 for a cannulated hip screw to femur 220 in both the anteroposterior and the lateral views. Guide pin 302 for cannulated hip screw 101 can then be inserted in the desired position with image guidance.

If reference bar 210 should be moved or loosened, registration can be done again during the operation just be repeating the two x-ray views. Once registration pin 215 is in place, identification of fiducials by the tedious method of touching points with a probe is unnecessary. The accuracy of image registration with registration pin 215 or other object is much greater than with previous methods.

What is claimed is:

1. An image guided surgery system comprising:
    an imaging device operable to obtain images of a region of a patient;
    a reference device operable to be positioned in the region of the patient, said reference device including at least one localization sensor being positioned on said reference device;
    a surgical instrument operable for use in performing an operation, said surgical instrument including at least one localization sensor positioned on said surgical instrument;
    a localization system operable to determine a position of said surgical instrument with respect to said reference device by use of said at least one localization sensor associated with said surgical instrument and said at least one localization sensor associated with said reference device; and
    only one fiducial marker for attachment to the region, said only one fiducial marker being visible in the image of the region of the patient, wherein said only one fiducial marker is used for determining the position of the region relative to the localization system.

2. The image guided surgery system as defined in claim 1 wherein said imaging device is a fluoroscopic imaging device.

3. The image guided surgery system as defined in claim 2 wherein said fluoroscopic imaging device is a C-arm fluoroscopic imaging device.

4. The image guided surgery system as defined in claim 3 wherein said C-arm fluoroscopic imaging device includes an x-ray generator and an x-ray receiver operable to obtain fluoroscopic images of the region of the patient.

5. The image guided surgery system as defined in claim 1 wherein said localizing sensors are emitters.

6. The image guided surgery system as defined in claim 5 wherein said emitters are optical emitters.

7. The image guided surgery system as defined in claim 6 wherein said optical emitters are LED optical emitters.

8. The image guided surgery system as defined in claim 1 wherein said localization system is an optical localization system.

9. The image guided surgery system as defined in claim 8 wherein said optical localization system includes an optical digitizer camera.

10. The image guided surgery system as defined in claim 1 wherein the region of the patient is an object bone in the patient.

11. The image guided surgery system as defined in claim 10 wherein said only one fiducial marker and a shape of the object bone is used for determining position of the object bone relative to the localization system.

12. The image guided surgery system as defined in claim 1 further comprising a computer programmed to match images from said imaging device to effect a two-dimensional image registration.

13. The image guided surgery system as defined in claim 1 further comprising a computer programmed for determining a plane in which a patient body lies in relation to said reference device.

14. The image guided surgery system as defined in claim 1 wherein said imaging device further includes at least one localization sensor being positioned on said imaging device and wherein said localization system is operable to determine a position of said imaging device.

15. The image guided surgery system as defined in claim 1 further comprising a monitor operable to display the images of the region of the patient and the position of said surgical instrument overlying the images in near real-time for continually monitoring a position of said surgical instrument.

16. The image guided surgery system as defined in claim 1 wherein said surgical instrument is a drill operable to drive a guide pin into the region of the patient.

17. The image guided surgery system as defined in claim 1 further comprising a computer programmed to reduce distortion in the images.

18. The image guided surgery system as defined in claim 1 further comprising a monitor to display the image of the region of the patient and a graphic representation of the position of said surgical instrument overlying the image, wherein the graphical representation includes an extended projection of said surgical instrument to determine correct trajectory of said surgical instrument.

19. The image guided surgery system as defined in claim 1 wherein said fiducial marker is a surgical implant.

20. The image guided surgery system as defined in claim 19 wherein the surgical implant is an intramedullary nail.

21. The image guided surgery system as defined in claim 1 further comprising a computer programmed to perform two-dimensional image registration by matching an outline of bone in two planes.

22. An image guided surgery system comprising:
    an imaging device operable to obtain images of an object bone of a patient, said imaging device including at least one localization sensor positioned on said imaging device;
    a reference device operable to be attached to the object bone, said reference device including at least one localization sensor positioned on said reference device;
    a surgical instrument operable for use in performing an operation, said surgical instrument including at least one localization sensor positioned on said surgical instrument;
    a localization system operable to determine a position of said imaging device, said surgical instrument and said reference device;
    a computer programmed to determine a real-time trajectory of said surgical instrument;
    a monitor operable to display the images of the object bone from said imaging device and the real-time position of said surgical instrument overlying the images for continually monitoring a position of said surgical instrument; and only one fiducial marker for attachment to the object bone, said one fiducial marker being visible in the image of the object bone, wherein said only one fiducial marker is used for determining the position of the object bone relative to the localization system.

23. The image guided surgery system as defined in claim 22 wherein said computer is programmed to overlay a graphic display of an implant having a predetermined length on the image of the object bone in near real-time.

24. The image guided surgery system as defined in claim 23 wherein said implant is a fixation device.

25. The image guided surgery system as defined in claim 22 wherein said imaging device is a fluoroscopic imaging device.

26. The image guided surgery system as defined in claim 25 wherein said fluoroscopic imaging device is a C-arm fluoroscopic imaging device.

27. The image guided surgery system as defined in claim 26 wherein said C-arm fluoroscopic imaging device includes an x-ray generator and an x-ray receiver operable to obtain fluoroscopic images of the region of the patient.

28. The image guided surgery system as defined in claim 22 wherein said localizing sensors are emitters.

29. The image guided surgery system as defined in claim 28 wherein said emitters are optical emitters.

30. The image guided surgery system as defined in claim 29 wherein said optical emitters are LED optical emitters.

31. The image guided surgery system as defined in claim 22 wherein said localization system is an optical localization system.

32. The image guided surgery system as defined in claim 31 wherein said optical localization system includes an optical digitizer camera.

33. The image guided surgery system as defined in claim 22 wherein said only one fiducial marker and a shape of the object bone is used for determining position of the object bone relative to the localization system.

34. The image guided surgery system as defined in claim 22 wherein said computer is programmed to match images from said imaging device to affect a two-dimensional image registration.

35. The image guided surgery system as defined in claim 22 wherein said computer is programmed to determine a plane in which a patient body lies in relation to said reference device.

36. The image guided surgery system as defined in claim 22 wherein said surgical instrument is a drill operable to drive a guide pin into the object bone of the patient.

37. The image guided surgery system as defined in claim 22 wherein said computer is programmed to reduce distortion in the images.

38. The image guided surgery system as defined in claim 22 wherein said fiducial marker is a surgical implant.

39. The image guided surgery system as defined in claim 38 wherein the surgical implant is an intramedullary nail.

40. The image guided surgery system as defined in claim 22 wherein said computer is programmed to perform two-dimensional image registration by matching an outline of the object bone in two planes.

41. An imaged guided surgery system comprising:
an imaging device operable to obtain images of an object bone of a patient;
a reference device operable to be attached to the object bone, said reference device including at least one localization sensor being positioned on said reference device;
a surgical instrument operable for use in performing an operation, said surgical instrument including at least one localization sensor positioned on said surgical instrument;
a localization system operable to determine a position of said surgical instrument with respect to said reference device by use of said at least one localization sensor associated with the surgical instrument and said at least one localization sensor associated with said reference device;
a computer programmed to perform two-dimensional image registration by matching an outline of the object bone in two planes from at least two images; and
only one fiducial marker for attachment to the object bone, said one fiducial marker being visible in the image of the object bone, wherein said only one fiducial marker is used for determining the position of the object bone relative to the localization system.

42. The image guided surgery system as defined in claim 41 wherein said computer is programmed to overlay a graphic display of an implant having a predetermined length on the image of the object bone in near real-time.

43. The image guided surgery system as defined in claim 42 wherein said implant is a fixation device.

44. The image guided surgery system as defined in claim 41 wherein said imaging device is a fluoroscopic imaging device.

45. The image guided surgery system as defined in claim 44 wherein said fluoroscopic imaging device is a C-arm fluoroscopic imaging device.

46. The image guided surgery system as defined in claim 45 wherein said C-arm fluoroscopic imaging device includes an x-ray generator and an x-ray receiver operable to obtain fluoroscopic images of the region of the patient.

47. The image guided surgery system as defined in claim 41 wherein said localizing sensors are emitters.

48. The image guided surgery system as defined in claim 47 wherein said emitters are optical emitters.

49. The image guided surgery system as defined in claim 48 wherein said optical emitters are LED optical emitters.

50. The image guided surgery system as defined in claim 41 wherein said localization system is an optical localization system.

51. The image guided surgery system as defined in claim 50 wherein said optical localization system includes an optical digitizer camera.

52. The image guided surgery system as defined in claim 41 wherein said only one fiducial marker and a shape of the object bone is used for determining position of the object bone relative to the localization system.

53. The image guided surgery system as defined in claim 41 wherein said computer is programmed to match images from said imaging device to affect the two-dimensional image registration.

54. The image guided surgery system as defined in claim 41 wherein said computer is programmed to determine a plane in which a patient body lies in relation to said reference device.

55. The image guided surgery system as defined in claim 41 wherein said imaging device further includes at least one localization sensor being positioned on said imaging device and wherein said localization system is operable to determine a position of said imaging device.

56. The image guided surgery system as defined in claim 41 further comprising a monitor operable to display the images of the region of the patient and the position of said surgical instrument overlying the images in near real-time for continually monitoring a position of said surgical instrument.

57. The image guided surgery system as defined in claim 41 wherein said surgical instrument is a drill operable to drive a guide pin into the object bone of the patient.

58. The image guided surgery system as defined in claim 41 wherein said computer is programmed to reduce distortion in the images.

59. The image guided surgery system as defined in claim 41 further comprising a monitor operable to display the image of the region of the patient and a graphic representation of the position of said surgical instrument overlying the image, wherein the graphical representation includes an extended projection of said surgical instrument to determine correct trajectory of said surgical instrument.

60. The image guided surgery system as defined in claim 41 wherein said only one fiducial marker is a surgical implant.

61. The image guided surgery system as defined in claim 60 wherein the surgical implant is an intramedullary nail.

62. The image guided surgery system as defined in claim 41 wherein said computer is programmed to determine a real-time trajectory of said surgical instrument.

63. An image guided system comprising:
an imaging device operable to obtain images of an object bone of a patient, said imaging device including at least one localization sensor positioned on said imaging device;
a reference device operable to be attached to the object bone, said reference device including at least one localization sensor positioned on said reference device;
a localization system operable to determine a position of said imaging device, a surgical instrument and said reference device;
a computer programmed to determine a real-time trajectory of said surgical instrument; and
only one fiducial marker for attachment to the object bone, said one fiducial marker being visible in the image of the object bone, wherein said only one fiducial marker is used for determining the position of the object bone relative to the localization system.

64. The image guided system of claim 63, further comprising:
a surgical instrument operable for use in performing an operation, said surgical instrument including at least one localization sensor positioned on said surgical instrument.

65. The image guided surgery system of claim 64, further comprising:
a monitor operable to display the images of the object bone from said imaging device and the real-time position of said surgical instrument overlying the images for continually monitoring a position of said surgical instrument.

* * * * *